US006329418B1

United States Patent
Cheng et al.

(10) Patent No.: US 6,329,418 B1
(45) Date of Patent: Dec. 11, 2001

(54) SUBSTITUTED PYRROLIDINE HYDROXAMATE METALLOPROTEASE INHIBITORS

(75) Inventors: Menyan Cheng, West Chester; Michael George Natchus, Glendale; Biswanath De, Cincinnati; Neil Gregory Almstead, Loveland; Yetunde Olabisi Taiwo, West Chester; Stanislaw Pikul, Mason, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/274,564

(22) Filed: Mar. 23, 1999

Related U.S. Application Data

(60) Provisional application No. 60/081,667, filed on Apr. 14, 1998.

(51) Int. Cl.[7] .................. A61K 31/40; A61K 31/405; C07D 207/22; C07D 207/48; C07D 239/24

(52) U.S. Cl. .................. 514/423; 548/517; 548/518; 548/519; 548/533; 548/537; 548/183; 548/230; 548/262.2; 548/314.7; 548/367.4; 544/96; 544/106; 544/238; 544/309; 544/330; 544/358; 546/184; 546/281.4; 514/228.8; 514/235.5; 514/252.06; 514/252.19; 514/256; 514/269; 514/315; 514/336; 514/365; 514/374; 514/383; 514/385

(58) Field of Search .................. 548/517, 518, 548/519, 533, 537, 183, 230, 262.2, 314.7, 367.4; 514/423, 228.8, 235.5, 252.06, 252.19, 256, 269, 315, 336, 354, 365, 374, 385; 544/96, 106, 238, 309, 330, 358; 546/184, 281.4

(56) References Cited

U.S. PATENT DOCUMENTS

| | | | |
|---|---|---|---|
| 3,380,992 | * | 4/1968 | Argoudellis et al. ................. 260/210 |
| 4,377,701 | * | 3/1983 | Natarajan et al. .................... 548/533 |
| 4,743,587 | | 5/1988 | Dickens et al. ....................... 514/575 |
| 4,771,038 | | 9/1988 | Wolanin et al. ........................ 514/18 |
| 4,996,358 | | 2/1991 | Handa et al. .......................... 562/621 |
| 5,183,900 | | 2/1993 | Galardy et al. ....................... 548/495 |
| 5,403,952 | | 4/1995 | Hagmann et al. ....................... 510/85 |
| 5,473,100 | | 12/1995 | Isomura et al. ......................... 562/26 |
| 5,506,242 | | 4/1996 | MacPherson et al. ................ 514/336 |

FOREIGN PATENT DOCUMENTS

| | | |
|---|---|---|
| 0276436B1 | 6/1993 | (EP) . |
| 0606046A1 | 7/1994 | (EP) . |

(List continued on next page.)

OTHER PUBLICATIONS

R.H. Andreatta, et al, "Synthesis of CIS and TRANS Isomers of 4–Chloro–$_L$–Proline, 4–Bromo–$_L$–Proline, and 4–Amino–$_L$–Proline", *Aust. J. Chem*, vol. 20, 1967, pp. 1493–1509.

E.M. Smith, et al, "Synthesis and Pharmacological Activity of Angiotensin Converting Enzyme Inhibitors: N–(Mercaptoacyl)–4–Substituted–(S)–Prolines", *J. Med. Chem.*, vol. 31, 1988, pp. 875–885.

R.M. Adlington, et al, "A Radical Route to 2(S)–4–Exomethylene Proline", *Tetrahedron*, vol. 48, No. 21, 1992, pp. 6529–6536.

D.E. Mullins et al., "The Role of Proteinase in Cellular Invasiveness", *Biochimica et Biophysica Acta*, vol. 695, 1983, pp; 177–214.

(List continued on next page.)

*Primary Examiner*—Mukund J. Shah
*Assistant Examiner*—Venkataraman Balasubramanian
(74) *Attorney, Agent, or Firm*—Carl J. Roof; James C. Kellerman; Tanaga A. Boozer

(57) ABSTRACT

The invention provides compounds which are potent inhibitors of metalloproteases and which are effective in treating conditions characterized by excess activity of these enzymes. In particular, the present invention relates to compounds having a structure according to the following Formula (I):

[chemical structure]

wherein $R_1$, $R_2$, X, Z, m, and n are defined below.

to This invention also includes optical isomers, diastereomers and enantiomers of the formula above, and pharmaceutically-acceptable salts, biohydrolyzable amides, esters, and imides thereof. The compounds of the present invention are useful for the treatment of diseases and conditions which are characterized by unwanted metalloprotease activity. Accordingly, the invention further provides pharmaceutical compositions comprising these compounds. The invention still further provides methods of treatment for metalloprotease-related maladies using these compounds or the pharmaceutical compositions containing them.

17 Claims, No Drawings

FOREIGN PATENT DOCUMENTS

| | | |
|---|---|---|
| 0684240A1 | 11/1995 | (EP) . |
| 0498665B1 | 4/1996 | (EP) . |
| 0575844B1 | 1/1998 | (EP) . |
| 0574758B1 | 9/1998 | (EP) . |
| 2268934A | 1/1994 | (GB) . |
| 2282598A | 4/1995 | (GB) . |
| 07304770-A | 5/1994 | (JP) . |
| 08053403-A | 6/1994 | (JP) . |
| WO 92/17460 | 10/1992 | (WO) . |
| WO 92/22523 | 12/1992 | (WO) . |
| WO 93/14112 | 7/1993 | (WO) . |
| WO 93/21942 | 11/1993 | (WO) . |
| WO 94/10990 | 5/1994 | (WO) . |
| WO 94/25434 | 11/1994 | (WO) . |
| WO 94/25435 | 11/1994 | (WO) . |
| WO 95/04033 | 2/1995 | (WO) . |
| 95 04718 * | 2/1995 | (WO) . |
| WO 95/09620 | 4/1995 | (WO) . |
| WO 95/09633 | 4/1995 | (WO) . |
| WO 95/12603 | 5/1995 | (WO) . |
| WO 95/13289 | 5/1995 | (WO) . |
| WO 95/19956 | 7/1995 | (WO) . |
| WO 95/19957 | 7/1995 | (WO) . |
| WO 95/19961 | 7/1995 | (WO) . |
| WO 95/19965 | 7/1995 | (WO) . |
| WO 95/22966 | 8/1995 | (WO) . |
| WO 95/23790 | 9/1995 | (WO) . |
| WO 95/24921 | 9/1995 | (WO) . |
| WO 95/26989 | 10/1995 | (WO) . |
| WO 95/29892 | 11/1995 | (WO) . |
| WO 95/32944 | 12/1995 | (WO) . |
| WO 95/33709 | 12/1995 | (WO) . |
| WO 95/33731 | 12/1995 | (WO) . |
| WO 95/35275 | 12/1995 | (WO) . |
| WO 95/35276 | 12/1995 | (WO) . |
| WO 96/00214 | 1/1996 | (WO) . |
| WO 96/06074 | 2/1996 | (WO) . |
| WO 97/20824 | 6/1997 | (WO) . |
| WO 98/08815 | 3/1998 | (WO) . |

OTHER PUBLICATIONS

R. Reich et al., "Effects of Inhibitors of Plasminogen Activator, Serine Proteinases, and Collagenase IV on the Invasion of Basement Membranes by Metastatic Cells". *Cancer Research*, vol. 48, 1988, pp. 3307–3312.

B. Henderson et al., "Design of Inhibitors of Articular Cartilage Destruction", *Drugs of the Future,* vol. 15, No. 5, 1990, pp. 495–508.

H.S. Rasmussen et al., "Matrix Metalloproteinase Inhibition as a Novel Anticancer Strategy: A Review with Special Focus on Balimastat and Marimastat", *Pharmacol. Ther,* vol. 75, No. 1, 1997, pp.69–75.

J. Bird et al., "Synthesis of Novel N–Phosphonoalkyl Dipeptide Inhibitors of Human Collagenase", *J. Med. Chem.,* vol. 37, 1994, pp. 158–169.

K. Gijbels et al., "Reversal of Experimental Autoimmune Encephalomyelitis with a Hydroxamate Inhibitor of Matrix Metalloproteases", *J. Clin. Invest.,* vol. 94, 1994, pp. 2177–2182.

T.G. Wolfsberg et al., "ADAM, a Novel Family of Membrane Proteins Containing A Disintegrin And Metalloprotease Domain: Multipotential Functions in Cell–Cell and Cell–Matrix Interactions" *The Journal of Cell Biology,* vol. 131, No. 2, 1995, pp. 275–278.

* cited by examiner

SUBSTITUTED PYRROLIDINE HYDROXAMATE METALLOPROTEASE INHIBITORS

CROSS REFERENCE

This application claims priority under Title 35, United States Code 119(e) from Provisional Application Ser. No. 60/081,667, filed Apr. 14, 1998.

TECHNICAL FIELD

This invention is directed to compounds which are useful in treating diseases associated with metalloprotease activity, particularly zinc metalloprotease activity.

BACKGROUND

A number of structurally related metalloproteases effect the breakdown of structural proteins. These metalloproteases often act on the intercellular matrix, and thus are involved in tissue breakdown and remodeling. Such proteins are referred to as metalloproteases or MPs. There are several different families of MPs, classified by sequence homology. Several families of known MPs, as well as examples thereof, are disclosed in the art.

These MPs include Matrix-Metallo Proteases (MMPs); zinc metalloproteases; many of the membrane bound metalloproteases; TNF converting enzymes; angiotensin-converting enzymes (ACEs); disintegrins, including ADAMs (See Wolfsberg et al, 131 *J. Cell Bio.* 275–78 October, 1995); and the enkephalinases. Examples of MPs include human skin fibroblast collagenase, human skin fibroblast gelatinase, human sputum collagenase, aggrecanse and gelatinase, and human stromelysin. Collagenase, stromelysin, aggrecanase and related enzymes are thought to be important in mediating the symptomatology of a number of diseases.

Potential therapeutic indications of MP inhibitors have been discussed in the literature. See for example, U.S. Pat. No. 5,506,242 (Ciba Geigy Corp.); U.S. Pat. No. 5,403,952 (Merck & Co.); PCT published application WO 96/06074 (British Bio Tech Ltd); PCT Publication WO 96/00214 (Ciba Geigy); WO 95/35275 (British Bio Tech Ltd); WO 95/35276 (British Bio Tech Ltd); WO 95/33731 (Hoffman-LaRoche); WO 95/33709 (Hoffman-LaRoche); WO 95/32944 (British Bio Tech Ltd); WO 95/26989 (Merck); WO 9529892 (DuPont Merck); WO 95/24921 (Inst. Opthamology); WO 95/23790 (SmithKline Beecham); WO 95/22966 (Sanofi Winthrop); WO 95/19965 (Glycomed); WO 95 19956 (British Bio Tech Ltd); WO 95/19957 (British Bio Tech Ltd); WO 95/19961 (British Bio Tech Ltd) WO 95/13289 (Chiroscience Ltd.); WO 95/12603 (Syntex); WO 95/09633 (Florida State Univ); WO 95/09620 (Florida State Univ.); WO 95/04033 (Celltech); WO 94/25434 (Celltech); WO 94/25435 (Celltech); WO 93/14112 ( Merck); WO 94/0019 (Glaxo); WO 93/21942 (British Bio Tech Ltd); WO 92/22523 (Res. Corp. Tech. Inc.); WO 94/10990 (British Bio Tech Ltd); WO 93/09090 (Yamanouchi); and British patents GB 2282598 (Merck) and GB 2268934 (British Bio Tech Ltd); Published European Patent Applications EP 95/684240 (Hoffman LaRoche); EP 574758 (Hoffman LaRoche); EP 575844 (Hoffman LaRoche); Published Japanese applications; JP 08053403 (Fujusowa Pharm. Co. Ltd.); JP 7304770 (Kanebo Ltd.); and Bird et al, *J. Med. Chem.*, vol. 37, pp. 158–69 (1994).

Examples of potential therapeutic uses of MP inhibitors include rheumatoid arthritis (Mullins, D. E., et al., *Biochim. Biophys. Acta.* (1983) 695.117–214); osteoarthritis (Henderson, B., et al., *Drugs of the Future* (1990) 15:495–508); cancer (Rasmussen and McCann, *Pharmacol Ther.*, vol 75 no. 1, pp. 69–75 (1997)); the metastasis of tumor cells (ibid, Broadhurst, M. J., et al., European Patent Application 276,436 (published 1987), Reich, R., et al., 48 *Cancer Res.* 3307–3312 (1988); multiple sclerosis (Gijbels et al, *J. Clin. Invest.*, vol. 94, pp. 2177–2182 (1994)); and various ulcerations or ulcerative conditions of tissue. For example, ulcerative conditions can result in the cornea as the result of alkali burns or as a result of infection by Pseudomonas aeruginosa, Acanthamoeba, Herpes simplex and vaccinia viruses.

Other examples of conditions characterized by undesired metalloprotease activity include periodontal disease, epidermolysis bullosa, fever, inflammation and scieritis (Cf. DeCicco et al, WO 95 29892 published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13, 1988 to Wolanin, et al.; U.S. Pat. No. 4,743,587, issued May 10, 1988 to Dickens, et al., European Patent Publication Number 575,844, published Dec. 29, 1993 by Broadhurst, et al.; International Patent Publication No. WO 93/09090, published May 13, 1993 by Isomura, et al.; World Patent Publication 92/17460, published Oct. 15, 1992 by Markwell et al.; and European Patent Publication Number 498,665, published Aug. 12, 1992 by Beckett, et al.

It would be advantageous to inhibit these metalloproteases in treating diseases related to unwanted metalloprotease activity. Though a variety of inhibitors have been prepared, there is a continuing need for potent matrix metalloprotease inhibitors useful in treating diseases associated with metalloprotease activity.

SUMMARY OF THE INVENTION

The invention provides compounds which are potent inhibitors of metalloproteases and which are effective in treating conditions characterized by excess activity of these enzymes. In particular, the present invention relates to compounds having a structure according to the following Formula (I):

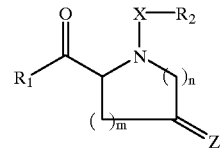

wherein $R_1$, $R_2$, X, Z, m, and n are defined below.

This invention also includes optical isomers, diastereomers and enantiomers of the formula above, and pharmaceutically-acceptable salts, biohydrolyzable amides, esters, and imides thereof.

The compounds of the present invention are useful for the treatment of diseases and conditions which are characterized by unwanted metalloprotease activity. Accordingly, the invention further provides pharmaceutical compositions comprising these compounds. The invention still further provides methods of treatment for metalloprotease-related maladies using these compounds or the pharmaceutical compositions containing them.

DETAILED DESCRIPTION

The compounds of the present invention are inhibitors of mammalian metalloproteases.

Terms and Definitions

The following is a list of definitions for terms used herein:

"Alkyl" is a saturated or unsaturated hydrocarbon chain having 1 to 15 carbon atoms, preferably 1 to 10, more preferably 1 to 4 carbon atoms. Alkyl chains may be straight or branched. Preferred branched alkyl have one or two branches, preferably one branch. Preferred alkyl are saturated. Unsaturated alkyl have one or more double bonds and/or one or more triple bonds. Preferred unsaturated alkyl have one or two double bonds or one triple bond, more preferably one double bond. Alkyl chains may be unsubstituted or substituted with from 1 to 4 substituents. Preferred substituted alkyl are mono-, di-, or trisubstituted. Alkyl may be substituted with halo, hydroxy, aryloxy (e.g., phenoxy), heteroaryloxy, acyloxy (e.g., acetoxy), carboxy, aryl (e.g., phenyl), heteroaryl, cycloalkyl, heterocycloalkyl, spirocycle, amino, amido, acylamino, keto, thioketo, cyano, or any combination thereof. Preferred alkyl groups include methyl, ethyl, propyl, isopropyl, butyl, vinyl, allyl, butenyl, and exomethylenyl.

Also, as referred to herein, a "lower" hydrocarbon moiety (e.g., "lower alkyl") is a hydrocarbon chain comprised of 1 to 6, preferably from 1 to 4, member atoms (carbon and heteroatoms if present).

"Aryl" is an aromatic hydrocarbon ring. Aryl rings are monocyclic or fused bicyclic ring systems. Monocyclic aryl rings contain 6 carbon atoms in the ring. Monocyclic aryl rings are also referred to as phenyl rings. Bicyclic aryl rings contain from 8 to 17 carbon atoms, preferably 9 to 12 carbon atoms in the ring. Bicyclic aryl rings include ring systems wherein one ring is aryl and the other ring is aryl, cycloalkyl, or heterocycloakyl. Preferred bicyclic aryl rings comprise 5-, 6- or 7-membered rings fused to 5-, 6-, or 7-membered rings. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, heteroaryloxy, or any combination thereof. Preferred aryl rings include naphthyl, tolyl, xylyl, and phenyl. The most preferred aryl ring radical is phenyl.

"Cycloalkyl" is a saturated or unsaturated hydrocarbon ring. Cycloalkyl rings are not aromatic. Cycloalkyl rings are monocyclic, or are fused, spiro, or bridged bicyclic ring systems. Monocyclic cycloalkyl rings contain from about 3 to about 9 carbon atoms, preferably from 3 to 7 carbon atoms in the ring. Bicyclic cycloalkyl rings contain from 7 to 17 carbon atoms, preferably from 7 to 12 carbon atoms in the ring. Preferred bicyclic cycloalkyl rings comprise 4-, 5-, 6- or 7-membered rings fused to 5-, 6-, or 7-membered rings. Cycloalkyl rings may be unsubstituted or substituted with from 1 to 4 substituents on the ring. Cycloalkyl may be susbstituted with halo, cyano, alkyl, heteroalkyl, haloalkyl, phenyl, keto, hydroxy, carboxy, amino, acylamino, aryloxy, heteroaryloxy, or any combination thereof. Preferred cycloalkyl rings include cyclopropyl, cyclopentyl, and cyclohexyl.

"Halo" is fluoro, chloro, bromo or iodo. Preferred halo are fluoro, chloro and bromo; more preferred are chloro and fluoro, especially fluoro.

"Haloalkyl" is a straight, branched, or cyclic hydrocarbon substituted with one or more halo substituents. Preferred haloalkyl are $C_1$–$C_{12}$; more preferred are $C_1$–$C_6$; more preferred still are $C_1$–$C_3$. Preferred halo substituents are fluoro and chloro. The most preferred haloalkyl is trifluoromethyl.

"Heteroalkyl" is a saturated or unsaturated chain containing carbon and at least one heteroatom, wherein no two heteroatoms are adjacent. Heteroalkyl chains contain from 2 to 15 member atoms (carbon and heteroatoms) in the chain, preferably 2 to 10, more preferably 2 to 5. For example, alkoxy (i.e., —O-alkyl or —O-heteroalkyl) radicals are included in heteroalkyl. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to 4 substituents. Preferred substituted heteroalkyl are mono-, di-, or trisubstituted. Heteroalkyl may be substituted with lower alkyl, halo, hydroxy, aryloxy, heteroaryloxy, acyloxy, carboxy, monocyclic aryl, heteroaryl, cycloalkyl, heterocycloalkyl, spirocycle, amino, acylamino, amido, keto, thioketo, cyano, or any combination thereof.

"Heteroatom" is a nitrogen, sulfur, or oxygen atom. Groups containing more than one heteroatom may contain different heteroatoms.

"Heteroaryl" is an aromatic ring containing carbon and from 1 to about 6 heteroatoms in the ring. Heteroaryl rings are monocyclic or fused bicyclic ring systems. Monocyclic heteroaryl rings contain from about 5 to about 9 member atoms (carbon and heteroatoms), preferably from 5 or 6 member atoms in the ring. Bicyclic heteroaryl rings contain from 8 to 17 member atoms, preferably 8 to 12 member atoms in the ring. Bicyclic heteroaryl rings include ring systems wherein one ring is heteroaryl and the other ring is aryl, heteroaryl, cycloalkyl, or heterocycloalkyl. Preferred bicyclic heteroaryl ring systems comprise 5-, 6- or 7-membered rings fused to 5-, 6-, or 7-membered rings. Heteroaryl rings may be unsubstituted or substituted with from 1 to 4 substituents on the ring. Heteroaryl may be substituted with halo, cyano, nitro, hydroxy, carboxy, amino, acylamino, alkyl, heteroalkyl, haloalkyl, phenyl, aryloxy, heteroaryloxy, or any combination thereof. Preferred heteroaryl rings include thienyl, thiazolo, imidazyl, purinyl, pyrimidyl, pyridyl, and furanyl.

"Heterocycloalkyl" is a saturated or unsaturated ring containing carbon and from 1 to about 4 (preferably 1 to 3) heteroatoms in the ring, wherein no two heteroatoms are adjacent in the ring and no carbon in the ring that has a heteroatom attached to it also has a hydroxyl, amino, or thiol radical attached to it. Heterocycloalkyl rings are not aromatic. Heterocycloalkyl rings are monocyclic, or are fused, bridged, or spiro bicyclic ring systems. Monocyclic heterocycloalkyl rings contain from about 4 to about 9 member atoms (carbon and heteroatoms), preferably from 5 to 7 member atoms in the ring. Bicyclic heterocycloalkyl rings contain from 7 to 17 member atoms, preferably 7 to 12 member atoms in the ring. Bicyclic heterocycloalkyl rings contain from about 7 to about 17 atoms, preferably from 7 to 12 atoms. Bicyclic heterocycloalkyl rings may be fused, spiro, or bridged ring systems. Preferred bicyclic heterocycloalkyl rings comprise 5-, 6- or 7-membered rings fused to 5-, 6-, or 7-membered rings. Heterocycloalkyl rings may be unsubstituted or substituted with from 1 to 4 substituents on the ring. Heterocycloalkyl may be substituted with halo, cyano, hydroxy, carboxy, keto, thioketo, amino, acylamino, acyl, amido, alkyl, heteroalkyl, haloalkyl, phenyl, phenoxy or any combination thereof. Preferred substituents on hetercycloalkyl include halo and haloalkyl.

"Spirocycle" is an alkyl or heteroalkyl diradical substituent of alkyl or heteroalkyl wherein said diradical substituent is attached geminally and wherein said diradical substituent forms a ring, said ring containing 4 to 8 member atoms (carbon or heteroatom), preferably 5 or 6 member atoms.

While alkyl, heteroalkyl, cycloalkyl, and heterocycloalkyl groups may be substituted with hydroxy, amino, and amido as stated above, the following are not envisioned in the invention:

1. Enols (OH attached to a carbon bearing a double bond).
2. Amino groups attached to a carbon bearing a double bond (except for vinylogous amides).
3. More than one hydroxy, amino, or amido attached to a single carbon (except where two nitrogen atoms are attached to a single carbon atom and all three atoms are member atoms within a heterocycloalkyl ring).
4. Hydroxy, amino, or amido attached to a carbon that also has a heteroatom attached to it.
5. Hydroxy, amino, or amido attached to a carbon that also has a halogen attached to it.

A "pharmaceutically-acceptable salt" is a cationic salt formed at any acidic (e.g., hydroxamic acid) group, or an anionic salt formed at any basic (e.g., amino) group. Many such salts are known in the art, as described in World Patent Publication 87/05297, Johnston et al., published Sep. 11, 1987 incorporated by reference herein. Preferred cationic salts include the alkali metal salts (such as sodium and potassium), and alkaline earth metal salts (such as magnesium and calcium) and organic salts. Preferred anionic salts include the halides (such as chloride salts), sulfonates, carboxylates, phosphates, and the like. Clearly contemplated in such salts are addition salts that may provide an optical center where once there was none. For example, a chiral tartrate salt may be prepared from the compounds of the invention, and this definition includes such chiral salts.

Such salts are well understood by the skilled artisan, and the skilled artisan is able to prepare any number of salts given the knowledge in the art. Furthermore, it is recognized that the skilled artisan may prefer one salt over another for reasons of solubility, stability, formulation ease and the like. Determination and optimization of such salts is within the purview of the skilled artisan's practice.

A "biohydrolyzable amide" is an amide of a metalloprotease inhibitor that does not interfere with the inhibitory activity of the compound, or that are readily converted in vivo by an animal, preferably a mammal, more preferably a human subject to yield an active metalloprotease inhibitor.

A "biohydrolyzable hydroxy imide" is an imide of a metalloprotease inhibitor that does not interfere with the metalloprotease inhibitory activity of these compounds, or that is readily converted in vivo by an animal, preferably a mammal, more preferably a human subject to yield an active metalloprotease inhibitor.

A "biohydrolyzable ester" is an ester of a metalloprotease inhibitor that does not interfere with the metalloprotease inhibitory activity of these compounds or that is readily converted by an animal to yield an active metalloprotease inhibitor.

A "solvate" is a complex formed by the combination of a solute (e.g., a metalloprotease inhibitor) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

"Optical isomer", "stereoisomer", and "diastereomer" as referred to herein have the standard art recognized meanings (Cf., *Hawley's Condensed Chemical Dictionary*, 11th Ed.). The illustration of specific protected forms and other derivatives of the compounds of the instant invention is not intended to be limiting. The application of other useful protecting groups, salt forms, etc. is within the ability of the skilled artisan.

As used herein, "mammalian metalloprotease" refers to the proteases disclosed in the "Background" of this application. Preferred "mammalian metalloproteases" include any metal-containing (preferably zinc-containing) enzyme found in animal, preferably mamalian sources capable of catalyzing the breakdown of collagen, gelatin or proteoglycan under suitable assay conditions. Appropriate assay conditions can be found, for example, in U.S. Pat. No. 4,743,587, which references the procedure of Cawston, et al., *Anal. Biochem.* (1979) 99:340–345, use of a synthetic substrate is described by Weingarten, H., et al., *Biochem. Biophy. Res. Comm.* (1984) 139:1184–1187. Any standard method for analyzing the breakdown of these structural proteins can, of course, be used. More prefered metalloprotease enzymes are zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

Compounds

The subject invention involves compounds having the following structure:

Formula (I)

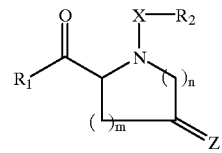

In the above structure, $R_1$ is OH, alkoxy, or $NR_3OR_3$, wherein each $R_3$ is independently selected from the group consisting of hydrogen, lower alkyl, and acyl. Preferred $R_1$ is OH and $NR_3OR_3$. Most preferred $R_1$ is NHOH.

In the above structure, X is $SO_2$, CO, $CO_2$, $CONR_5$, $POR_5$, or a covalent bond, wherein $R_5$ is hydrogen, alkyl, heteroalkyl, aryl, heteroaryl, cycloalkyl, heterocycloalkyl, aryloxy, or heteroaryloxy. Preferred $R_5$ is hydrogen and lower alkyl. Preferred X is $SO_2$ and $POR_5$. Most preferred X is $SO_2$.

In the above structure, $R_2$ is hydrogen, alkyl, heteroalkyl, aryl, heteroaryl, cycloalkyl, heterocycloalkyl, aryloxy or heteroaryloxy. Preferred $R_2$ is aryl and heteroaryl.

In the above structure, Z is (i) N—W, wherein n is at least 1 and W is aryl, heteroaryl, cycloalkyl, heterocycloalkyl, cycloalkenyl, or heterocycloalkenyl (ii) N—$OR_4$, N—$SR_4$, N—$NR_4R_4$, or N—$CR_4R_4R_4$, wherein n is at least 1 and each $R_4$ is independently hydrogen, alkyl, heteroalkyl, aryl, heteroaryl, cycloalkyl, heterocycloalkyl, cycloalkenyl, or heterocycloalkenyl

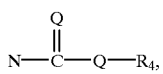
(iii)

wherein n is at least 1 and each Q is independently S or O

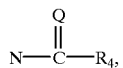
(iv)

wherein n is at least 1 (v) $CR_6R_6$, wherein each $R_6$ is independently hydrogen, halo, alkyl, heteroalkyl, aryl, heteroaryl, cycloalkyl, heterocycloalkyl, cycloalkenyl, or heterocycloalkenyl (vi) a ring, wherein said ring is cycloalkyl, heterocycloalkyl, cycloalkenyl, or heterocycloalkenyl

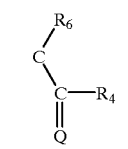
(vii)

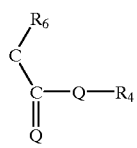
(viii)

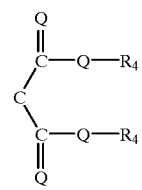
(ix)

(x) $C=CR_4R_4$ or (xi) $C=V$, wherein V is cycloalkyl, heterocycloalkyl, cycloalkenyl, and heterocycloalkenyl. Preferred Z is $N—OR_4$, $N—SR_4$, $N—NR_4R_4$, $N—CR_4R_4R_4$,

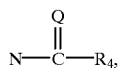

wherein n is at least 1; $CR_6R_6$; and a ring, wherein said ring is cycloalkyl, heterocycloalkyl, cycloalkenyl, or heterocycloalkenyl.

In the above structure, m and n are integers independently selected from 0 to about 4 and m+n is from about 2 to about 7. Preferred m is 1 and preferred n is 1. Most preferred m+n is 2.

The invention also includes optical isomers, diastereomers and enantiomers, and pharmaceutically-acceptable salts, solvates, biohydrolyzable amides, esters, or imides thereof.

Compound Preparation

The compounds of the invention can be prepared using a variety of procedures. The starting materials used in preparing the compounds of the invention are known, made by known methods, or are commercially available. Particularly preferred syntheses are the following two general reaction schemes:

Scheme 1

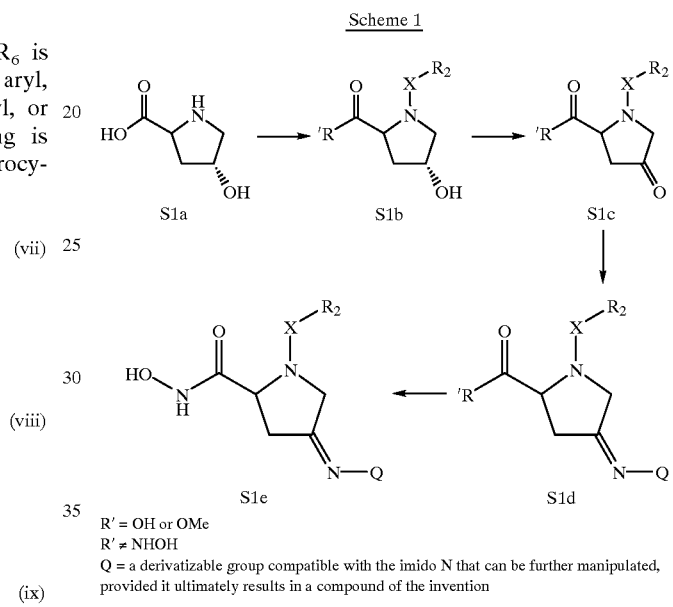

R' = OH or OMe
R' ≠ NHOH
Q = a derivatizable group compatible with the imido N that can be further manipulated, provided it ultimately results in a compound of the invention In Scheme 1, $R_1$, $R_2$, and X are as defined above. The 4-hydroxyproline (S1a) depicted as starting material for Scheme 1 is commercially available (such as from Aldrich).

In the above Scheme 1, 4-hydroxyproline (S1a) is coupled with a desired acyl derivative of choice using any of the commonly known methods to give (S1b). The subsequent oxidation step may be carried out using a number of methods well known to the skilled artisan including Jones oxidation and Swern-type manipulations to give ketones of type S1c.

The conversion of ketone S1c to compounds of type S1d is accomplished via a variety of well known methods depending upon the specific compound which is desired. For example, when Q=OH, hydroxyl amine derivatives (O-substituted or unsubstituted) are condensed with ketone S1c under acidic conditions to give the desired oxime derivatives. In the case where Q =N, hydrazones of type R"R"N—$NH_2$ are condensed with ketone S1c to give hydrazones of type S1d.

The final conversion to S1e can be accomplished using many coupling procedures well known to the skilled artisan including treatment of methyl ester with basic hydroxyl amine.

Scheme 2

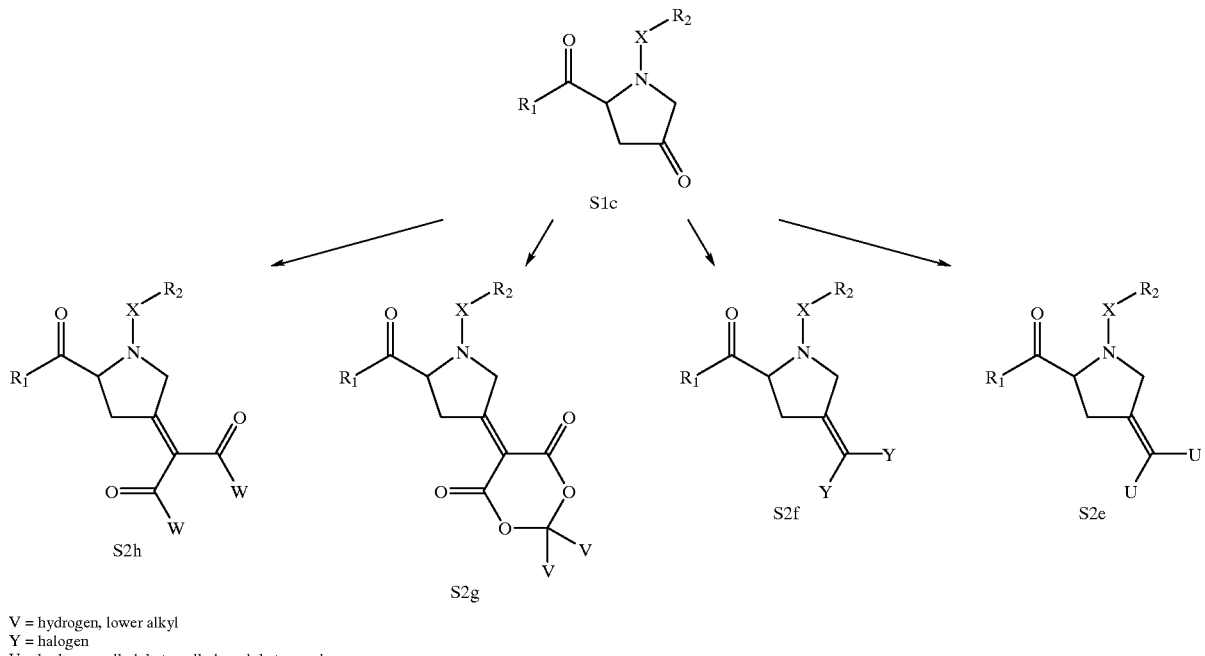

V = hydrogen, lower alkyl
Y = halogen
U = hydrogen, alkyl, heteroalkyl, aryl, heteroaryl The ketone S1c from Scheme 1 above can also be converted into compounds of type S2e, S2f, S2g, and S2h. Compounds of type S2e are prepared from ketone S1c using a Wettig, Peterson, or other commonly used olefination procedure. Compounds of type S2f are prepared from ketone S1c using well known methods such as those described in *J. Chem. Soc., Chem. Commun.*, 1972, 443 and *Tetrahedron Lett.* 1990, 31, 5571. Compounds of type S2g and S2h are prepared from ketone S1c using well known condensation methods with maonate type structures such as those described in *Synthesis*, 1978, 385 and *Tetrahedron*, 1993,49, 6821.

Compounds wherein m+n>2 can be made according to the reaction scheme above where S1a, S1b or S1c is substituted with a known compound of the appropriate ring size. For example, 4-ketopipecolic acid can be prepared as described by J-P. Obrecht et.al. in *Organic Synthesis* (1992), p.200.

A variety of compounds can be generated in a similar fashion, using the guidance of the schemes above.

It is recognized that it is preferable to use a protecting group for any reactive functionality such as a carboxyl, hydroxyl and the like, during the formation of the sultamester. This is standard practice, well within the normal practice of the skilled artisan.

In the above scheme, where R is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281).

These steps may be varied to increase yield of desired product. The skilled artisan will recognize the judicious choice of reactants, solvents, and temperatures is an important component in any successful synthesis. Determination of optimal conditions, etc. is routine. Thus the skilled artisan can make a variety of compounds using the guidance of the scheme above.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and other art that the skilled artisan is aware of.

The skilled artisan will readily appreciate that certain reactions are best carried out when other potentially reactive functionalities on the molecule is masked or protected, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Methods of Use

Metalloproteases (MPs) found in the body operate, in part, by breaking down the extracellular matrix, which comprises extracellular proteins and glycoproteins. Inhibitors of metalloproteases are useful in treating diseases caused, at least in part, by the breakdown of such proteins and glycoproteins. These proteins and glycoproteins play an important role in maintaining the size, shape, structure and stability of tissue in the body. Thus, MPs are intimately involved in tissue remodeling.

As a result of this activity, MPs have been said to be active in many disorders involving either the: (1) breakdown of tissues including degenerative diseases, such as arthritis, multiple sclerosis and the like; and metastasis or mobility of tissues in the body; or (2) remodeling of tissues including fibrotic disease, scarring, benign hyperplasia, and the like.

The compounds of the present invention treat disorders, diseases and/or unwanted conditions which are characterized by unwanted or elevated activity by MPs. For example, the compounds can be used to inhibit MPs which:

1. destroy structural proteins (i.e. the proteins that maintain tissue stability and structure);
2. interfere in inter/intracellular signaling, including those implicated in cytokine up-regulation, and/or cytokine processing and/or inflammation, tissue degradation and other maladies [Mohler K M, et al, Nature 370 (1994) 218–220, Gearing A J H, et al, Nature 370 (1994) 555–557 McGeehan G M, et al, Nature 370 (1994) 558–561]; and
3. facilitate processes which are undesired in the subject being treated, for example, the processes of sperm maturation, egg fertilization and the like.

As used herein, an "MP related disorder" or "MP related disease" is one that involves unwanted or elevated MP activity in the biological manifestation of the disease or disorder; in the biological cascade leading to the disorder; or as a symptom of the disorder. This "involvement" of the MP includes:

1. The unwanted or elevated MP activity as a "cause" of the disorder or biological manifestation, whether the activity was elevated genetically, by infection, by autoimmunity, trauma, biomechanical causes, lifestyle [e.g. obesity] or by some other cause;
2. The MP as part of the observable manifestation of the disease or disorder. That is, the disease or disorder is measurable in terms of the increased MP activity. From a clinical standpoint, unwanted or elevated MP levels indicate the disease, however, MPs need not be the "hallmark" of the disease or disorder; or
3. The unwanted or elevated MP activity is part of the biochemical or cellular cascade that results or relates to the disease or disorder. In this respect, inhibition of the MP activity interrupts the cascade, and thus controls the disease.

Advantageously, many MPs are not distributed evenly throughout the body. Thus, the distribution of MPs expressed in various tissues are often specific to those tissues. For example, the distribution of metalloproteases implicated in the breakdown of tissues in the joints is not the same as the distribution of metalloproteases found in other tissues. Though not essential for activity or efficacy, certain diseases, disorders, and unwanted conditions preferably are treated with compounds that act on specific MPs found in the affected tissues or regions of the body. For example, a compound which displays a higher degree of affinity and inhibition for a MP found in the joints (e.g. chondrocytes) would be preferred over another compound which is less specific when treating a disease, disorder, or unwanted condition involving the joints.

In addition, certain inhibitors are more bioavialable to certain tissues than others. Choosing an MP inhibitor which is more bioavailable to a certain tissue and which acts on the specific MPs found in that tissue, provides for specific treatment of the disease, disorder, or unwanted condition. For example, compounds of this invention vary in their ability to penetrate into the central nervous system. Thus, compounds may be selected to produce effects mediated through MPs found specifically outside the central nervous system.

Determination of the specificity of an inhibitor of a specific MP is within the skill of the artisan in that field. Appropriate assay conditions can be found in the literature. Specifically, assays are known for stromelysin and collagenase. For example, U.S. Pat. No. 4,743,587 references the procedure of Cawston, et al., Anal Biochem (1979) 99:340–345. The use of a synthetic substrate in an assay is described by Weingarten, H., et al., Biochem Biophy Res Comm (1984) 139:1184–1187. Any standard method for analyzing the breakdown of structural proteins by MPs can, of course, be used. The ability of compounds of the invention to inhibit metalloprotease activity can, of course, be tested in the assays found in the literature, or variations thereof. Isolated metalloprotease enzymes can be used to confirm the inhibiting activity of the invention compounds, or crude extracts which contain the range of enzymes capable of tissue breakdown can be used.

The compounds of this invention are also useful for prophylactic or acute treatment. They are administered in any way the skilled artisan in the fields of medicine or pharmacology would desire. It is immediately apparent to the skilled artisan that preferred routes of administration will depend upon the disease state being treated and the dosage form chosen. Preferred routes for systemic administration include administration perorally or parenterally.

However, the skilled artisan will readily appreciate the advantage of administering the MP inhibitor directly to the affected area for many diseases, disorders, or unwanted conditions. For example, it may be advantageous to administer MP inhibitors directly to the area of the disease, disorder, or unwanted condition such as in the area affected by surgical trauma (e. g., angioplasty), scarring, or burning (e.g., topical to the skin), Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, arrhythmia, angioplasty restenosis and aortic aneurysm may increase long term success of any other treatment, or may be a treatment in itself.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultraviolet damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scieroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus; CMV retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping to premature labor and delivery.

Since MPs are implicated in the inflammatory response, and in the processing of cytokines the compounds are also useful as anti-inflammatories, for use in disease where inflammation is prevalent including inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumitoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the matrix metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

Compositions

The compositions of the invention comprise:

(a) a safe and effective amount of a compound of the invention; and (b) a pharmaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences,* Mack Publishing Company, Easton, Pa., latest edition.

A "safe and effective amount" of a Formula (I) compound is an amount that is effective, to inhibit metalloproteases at the site(s) of activity, in an animal, preferably a mammal, more preferably a human subject, without undue adverse side effects (such as toxicity, irritation, or allergic response), commensurate with a reasonable benefit/risk ratwhen used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to an animal, preferably a mammal, more preferably a human. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably a mammal, more preferably a human being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as Tweens; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with a blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "ced" is a composition of this invention containing an amount of a Formula (I) compound that is suitable for administration to an animal, preferably a mammal, more preferably a human subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics,* Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emollients, emulsifiers, thickening agents, solvents and the like.

Methods of Administration

This invention also provides methods of treating or preventing disorders associated with excess or undesired metalloprotease activity in a human or other animal subject, by administering a safe and effective amount of a Formula (I) compound to said subject. As used herein, a "disorder associated with excess or undesired metalloprotease activity" is any disorder characterized by degradation of matrix proteins. The methods of the invention are useful in treating disorders described above.

Compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the metalloprotease is accumulated by using targeting ligands. For example, to focus the inhibitors to metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases. Some bacterial metalloproteases may be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

Preparation and Use of Antibodies

Metalloproteases active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

The invention compounds can also be coupled to labels such as scintigraphic labels, e.g., technetium 99 or I-131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, and uses of the present invention.

EXAMPLES

Compounds are analyzed using $^1H$ and $^{13}C$ NMR, Elemental analysis, mass spectra and/or IR spectra, as appropriate.

Typically tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merk) as appropriate. Thin layer chromatography analysis (TLC) is performed on glass mounted silica gel plates (200–300 mesh; Baker) and visualized with UV or 5% phosphomolybdic acid in EtOH.

Examples 1–13

The following chart shows the structure of compounds exemplified in Examples 1–13:

| Example | A | B |
|---|---|---|
| 1 | —$CH_3$ | —H |
| 2 | —$CH_2CH_2CH_2CH_3$ | —H |
| 3 | —$CH_3$ | —$CH_3$ |
| 4 | —$CH_2CH_3$ | —$CH_3$ |
| 5 | —$CHCH_2CH_3$ | —$CH_3$ |
| 6 | —$CH_2CH_2CH_2CH_3$ | —$CH_3$ |
| 7 | —Ph | —$CH_3$ |
| 8 | 4-$C_6H_4F$ | —$CH_3$ |
| 9 | 4-Pyr | —$CH_3$ |
| 10 | —$CH_2CH_2CH_2CH_3$ | —$CH_2CH_3$ |
| 11 | —$CH_3$ | —$C(CH_3)_3$ |
| 12 | —$CH_2CH_2CH_2CH_3$ | —$C(CH_3)_3$ |
| 13 | 4-$C_6H_4F$ | —$C(CH_3)_3$ |

Ph—phenyl
$C_6H_4$-phenyl diradical
—O—A corresponds to a substituent of $R_2$ in Formula (I) when $R_2$ is phenyl.
—O—B corresponds to $R_4$ in Formula (I) when Z is N—$OR_4$.

Example 1

Preparation of N-Hydroxy-1N-(4-methoxyphenyl) sulfonyl-4-(Z,E-N-hydroxyimino)pyrrolidine-2R-carboxamide a. Methyl-1N-(4-methoxyphenylsulfonyl)-4(R)-hydroxy-pyrrolidine-2(R)-carboxylate (1a): cis-Hydroxy-D-proline (50 g, 0.38 mole) is dissolved in water:dioxane (1:1, 300 mL) with triethylamine (135 mL, 0.96 mole). The 4-methoxyphenylsulfonyl chloride (87 g, 0.42 mole) is added along with 2,6-dimethylaminopyridine (4.6 g, 0.038 mole) and the mixture is stirred for 14 hours at room temperature. The mixture is then concentrated and diluted with EtOAc. The layers are separated and the organic layer is washed twice with 1 N HCl, once with brine, dried over $MgSO_4$, filtered and evaporated to give solid material which is dissolved in MeOH (500 mL). Thionyl chloride (50 mL) is added dropwise and the resulting mixture is stirred for 14 hours. The mixture is then evaporated to dryness and triturated with CHCl3 to give 1a which is sufficiently pure to carry forward without purification.

b. Methyl-1N-(4-methoxyphenylsulfonyl)-4-oxo-pyrrolidine-2(R)-carboxylate (1b): A 0.76 M batch of Jones reagent is prepared. The alcohol 1a (10.0 g, 31.7 mmoles) is dissolved in 175 mL of acetone and cooled to 0° C. Jones reagent is added (20 mL, 317 mmoles) and the mixture is stirred at room temperature for 14 hours. The reaction mixture is diluted with water and extracted three times with EtOAc. The organic layers are washed three times with water and once with sodium chloride, dried over $MgSO_4$, and evaporated. Purification of the product by chromatography on silica gel using EtOAc: hexane (1:1) provides the ketone 1b.

c. The compound of 1b (0.2 g, 0.6 mmol) is mixed with $NH_2OK$ (3 mL, 5.1 mmol, 1.7 M in methanol as described in Fieser and Fieser, Vol 1, p 478) and stirred overnight at room temperature. Acidified with 1N HCl, the mixture is extracted three times with EtOAc. The combined EtOAc layer is dried over $MgSO_4$ and concentrated under reduced pressure. The crude product is purified by reverse phase prep HPLC (60A40B, A, 95% $H_2O$, 5% acetonitrile, 0.1% formic acid; B, 80% acetonitrile, 20% $H_2O$; 19×300 mm waters SymmetryPrep C18 column) to give Example 1.

Example 2

Preparation of Hydroxy 1N-(4-n-butoxyphenyl) sulfonyl-4-(Z,E-N-hydroxyimino)pyrrolidine-2R-carboxamide a. Methyl-1N-(4-n-butoxyphenylsulfonyl-(4R)-hydroxy-pyrrolidine-(2R)-carboxylate (2a): cis-4-Hydroxy-D-proline (14.8 g, 112.95 mmole) is mixed with water:dioxane (1:1, 90 mL), triethylamine (39.3 mL, 282 mmole) and N-dimethylaminopyridine (1.3 g, 11.3 mmole). The 4-(n-butoxy)phenylsulfonyl chloride (29.5 g, 118.6 mmole) is added and the mixture is stirred for 14 hours at room temperature. The mixture is then concentrated and diluted with EtOAc and 1N HCl. The layers are separated and the organic layer is washed twice with 1N HCl, once with brine, dried over $MgSO_4$, filtered and evaporated to give solid material which is dissolved in MeOH (200 mL). Thionyl chloride (20 mL, 272 mmole) is added dropwise and the resulting mixture is stirred for 14 hours. The mixture is then evaporated to dryness to give 2a which is sufficiently pure to carry forward without purification.

b. Methyl-1N-(4-butoxyphenylsulfonyl)-4-oxo-pyrrolidine-2(R)-carboxylate (2b): A 8N solution of Jones reagent is prepared (see e.g. Oxidations in Organic Chemistry, P273). The alcohol 2a (40 g, 112 mmol) is dissolved in 300 mL of acetone and cooled to 0° C. Jones reagent is added (120 mL, 960 mmol) (color changed from orange-red to green) and the mixture is stirred at room temperature for 14 hours. The reaction mixture is diluted with water and extracted three times with EtOAc. The organic layers are washed three times with water and once with sodium chloride, dried over $MgSO_4$, and evaporated. The product is crystallized from EtOAc to give 2b.

c. The compound of 2b (0.29 g, 0.8 mmol) is mixed with $NH_2OK$ (4 mL, 6.4 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by reverse phase prep HPLC (60A40B, A, 95% $H_2O$, 5% acetonitrile, 0.1% formic acid; B, 80% acetonitrile, 20% $H_2O$; 19×300 mm waters SymmetryPrep C18 column) to give Example 2.

Example 3

Preparation of N-Hydroxy 1N-(4-Methoxyphenyl) sulfonyl-4-(Z,E-N-methoxyimino)pyrrolidine-2R-carboxamide a. Methyl-1N-(4-methoxyphenyl)sulfonyl-4-(Z,E-N-methoxyimino)pyrrolidine-2R-carboxylate (3a): To a solution of 1a (15.0 g, 47.88 mmol) in dioxane (140 mL), methanol (70 mL) and water (40 mL), is added methoxylamine hydrochloride (12.2 g, 144 mmol) and sodium acetate (39.2 g, 479 mmol). The mixture is stirred overnight at room temperature, and diluted with water. The reaction mixture is extracted three times with EtOAc. The combined EtOAc layer is washed with brine, dried over $MgSO_4$, and concentrated under reduced pressure to give a mixture of isomers (Z/E) of 3a.

b. The compound of 3a (16.3 g, 47.8 mmol) is mixed with $NH_2OK$ (125 mL, 225 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by column eluting with $CH_2Cl_2:CH_3OH$ (95:5) to give Example 3.

Example 4

Preparation of N-Hydroxy 1N-(4-ethoxyphenyl) sulfonyl-4-(Z,E-N-methoxyimino)pyrrolidine-2R-carboxamide a. Methyl-1N-(4-ethoxyphenylsulfonyl)-4-oxo-pyrrolidine-2(R)-carboxylate (4a): The intermediate 4a is prepared using a method substantially similar to that above for the preparation of the intermediate 1a, substituting the appropriate starting material. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

b. Methyl-1N-(4-ethoxyphenyl)sulfonyl-4-(Z,E-N-methoxyimino)pyrrolidine-2R-carboxylate (4b): To a solution of ketone 4a (1.2 g, 3.67 mmol) in dioxane (10 mL), and methanol (5 mL) and water (5 mL), is added methoxylamine hydrochloride (0.77 g, 9.16 mmol) and sodium acetate (2.9 g, 36 mmol). The mixture is stirred overnight at room temperature, and diluted with water. The reaction mixture is extracted three times with EtOAc. The combined EtOAc layer is washed with brine, dried over $MgSO_4$, and concentrated under reduced pressure to give a mixture of isomers (Z/E) of 4b.

c. The compound of 4b (1.2 g, 3.37 mmol) is mixed with NH2OK (11.0 mL, 18.7 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by column eluting with EtOAc/hexane (7:3) to give Example 4.

Example 5

Preparation of N-Hydroxy 1N-(4-propoxyphenyl) sulfonyl-4-(Z,E-N-methoxyimino)pyrrolidine-2R-carboxamide a. Methyl-1N-(4-propoxyphenylsulfonyl)-4-oxo-pyrrolidine-2(R)-carboxylate (5a): The intermediate 5a is prepared using a method substantially similar to that above for the preparation of the intermediate 1a, substituting the appropriate starting material. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

b. Methyl-1N-(4-n-propoxyphenyl)sulfonyl-4-(Z,E-N-methoxyimino)pyrrolidine-2R-carboxylate (5b): To a solution of ketone 5a (0.8 g, 2.34 mmol) in dioxane (8 mL), and methanol (4 mL), is added methoxylamine hydrochloride (2 mL, 7 mmol, 30% solution in water) and sodium acetate (1.9 g, 23.4 mmol). The mixture is stirred overnight at room temperature, and diluted with water. The reaction mixture is extracted three times with EtOAc. The combined EtOAc layer is washed with brine, dried over $MgSO_4$, and concentrated under reduced pressure to give a mixture of isomers (Z/E) of 5b.

c. The compound of 5b (0.9 g, 2.43 mmol) is mixed with $NH_2OK$ (7.2 mL, 12.1 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by column eluting with EtOAc/hexane (2:1) to give Example 5.

Example 6

Preparation of N-Hydroxy 1N-(4-n-butoxyphenyl) sulfonyl-4-(Z,E-N-methoxyimino)pyrrolidine-2R-carboxamide a. Methyl-1N-(4-n-butoxyphenyl)sulfonyl-4-(Z,E-N-methoxyimino)pyrrolidine-2R-carboxylate (6a): To a solution of 2a (2.0 g, 5.63 mmol) in dioxane (20 mL), and methanol (5 mL) and water (5 mL), is added methoxylamine hydrochloride (1.41 g, 16.9 mmol) and sodium acetate (4.6 g, 56.3 mmol). The mixture is stirred overnight at room temperature, and diluted with water. The reaction mixture is extracted three times with EtOAc. The combined EtOAc layer is washed with brine, dried over $MgSO_4$, and concentrated under reduced pressure to give a mixture of isomers (Z/E) of 6a.

b. The compound 6a (1.0 g, 4.95 mmol) is mixed with $NH2OK$ (13.8 mL, 24.7 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by column eluting with $CH_2Cl_2$:$CH_3OH$ (95:5) to give Example 6.

Example 7

Preparation of N-Hydroxy 1N-(4-phenoxyphenyl) sulfonyl-4-(Z,E-N-methoxyimino)pyrrolidine-2R-carboxamide a. 1N-(4-Phenoxyphenyl)sulfonyl-4R-hydroxy-pyrrolidine-2R-carboxylic acid (7a): To a solution of cis-4-hydroxy-D-proline (5.85 g, 44.7 mmol) in dioxane (20 mL), water (20 mL), triethyl amine (15.6 mL, 111.7 mmol), and 4-dimethylaminopyridine (0.54 g, 4.4 mmol) at 0° C. is added 4-phenoxybenzene sulfonyl chloride (11.5 g, 43 mmol) slowly. The mixture is stirred overnight at room temperature and diluted with 1N HCl. The reaction mixture is extracted three times with EtOAc. The combined EtOAc layer is washed with brine, dried over $MgSO_4$, and concentrated under reduced pressure to give 7a.

b. Methyl-1N-(4-phenoxyphenyl)sulfonyl-4R-hydroxy-pyrrolidine-2R-carboxylate (7b): To a solution of acid 7a (14.6 g, 40.19 mmol) in methanol (75 mL) is added thionyl chloride (7.3 mL, 100 mmol) dropwise. The mixture is stirred 1 hour at 45° C. and overnight at room temperature. The solvent is removed under reduced pressure to give 7b as a thick oil.

c. Methyl-1N-(4-phenoxyphenyl)sulfonyl-4-oxo-pyrrolidine-2R-carboxylate (7c): To a solution of alcohol 7b (14.8 g, 39.2 mmol) in acetone (110 mL) is added Jone's reagent (28 mL, 224 mmol, 8N solution prepared as described in Oxidation in Org. Chem., Vol 186, P273). The mixture is stirred overnight at room temperature. The green solid formed is removed by filtration, and the solvent is removed under reduced pressure. The reaction mixture is then dissolved in water and extracted three times with EtOAc. The combined EtOAc layer is washed twice with water, once with brine, dried over $MgSO_4$, and concentrated under reduced pressure to give 7c.

d. Methyl-1N-(4-phenoxyphenyl)sulfonyl-4-(Z,E-N-methoxyimino)pyrrolidine-2R-carboxylate (7d): To a solution of ketone 7c (1.5 g, 4 mmol) in dioxane (15 mL), and methanol (5 mL) and water (5 mL), is added methoxylamine hydrochloride (1.02 g, 12 mmol) and sodium acetate (3.28 g, 40 mmol). The mixture is stirred overnight at room temperature and diluted with water. The reaction mixture is extracted three times with EtOAc. The combined EtOAc layer is washed with brine, dried over MgSO4, and concentrated under reduced pressure. The crude product is purified by column eluting with hexane : EtOAc (4:1) to give a mixture of isomers (Z/E) of 7d.

e. The compound of 7d (0.6 g, 1.49 mmol) is mixed with $NH2OK$ (4.2 mL, 7.4 mmol, 1.7 M in methanol solution prepared as described in Fieser and Fieser, Vol 1, p 478) and stirred overnight at room temperature. Acidified with 1N HCl, the mixture is extracted three times with EtOAc. The combined EtOAc layer is dried over $MgSO_4$ and concentrated under reduced pressure. The crude product is purified by reverse phase prep HPLC (55A45B, A, 95% $H_2O$, 5% acetonitrile, 0.1% formic acid; B, 80% acetonitrile, 20% $H_2O$; 19×300 mm waters SymmetryPrep C18 column) to give Example 7.

Example 8

Preparation of N-Hydroxy 1N-[4-(4-Fluorophenoxy)phenyl]sulfonyl-4-(Z,E-N-methoxyimino)pyrrolidine-2R-carboxamide a. 1N-[4-(4-Fluorophenoxy)phenyl]sulfonyl-4R-hydroxy-pyrrolidine-2R-carboxylic acid (8a): To a solution of cis-4-hydroxy-D-proline (4.97 g, 37.9 mmol) in dioxane (20 mL), water (20 mL), triethyl amine (23 mL, 165 mmol), and 4-dimethylaminopyridine (0.43 g, 3.6 mmol) at 0° C. is added 4-phenoxybenzene sulfonyl chloride (10 g, 36.1 mmol) slowly. The mixture is stirred overnight at room temperature and diluted with 1N HCl. The reaction mixture is extracted three times with EtOAc. The combined EtOAc layer is washed with brine, dried over $MgSO_4$, and concentrated under reduced pressure to give 8a.

b. Methyl-1N-[4-(4-Fluorophenoxy)phenyl]sulfonyl-4R-hydroxy-pyrrolidine -2R-carboxylate (8b): To a solution of acid 8a (11.5 g, 30.1 mmol) in methanol (100 mL) is added thionyl chloride (13 mL, 180 mmol) dropwise. The mixture is stirred for 1 hour at 50° C. and overnight at room temperature. The solvent is removed under reduced pressure to give 8b.

c. Methyl-1N-[4-(4-Fluorophenoxy)phenyl]sulfonyl-4-oxo-pyrrolidine-2R-carboxylate (8c): To a solution of alcohol 8b (10 g, 25.3 mmol) in acetone (80 mL) is added Jone's reagent (13 mL, 101 mmol, 8N solution prepared as described in Oxidation in Org. Chem., Vol 186, P273). The mixture is stirred overnight at room temperature. The green solid formed is removed by filtration and the solvent removed under reduced pressure. The reaction mixture is then dissolved in water, and extracted three times with EtOAc. The combined EtOAc layer is washed twice with water, once with brine, dried over $MgSO_4$, and concentrated under reduced pressure to give 8c.

d. Methyl-1N-[4-(4-Fluorophenoxy)phenyl]sulfonyl-4-(Z, E-N-methoxyimino)pyrrolidine-2R-carboxylate (8d): To a solution of ketone 8c (0.9 g, 2.29 mmol) in dioxane (8 mL), methanol (5 mL) and water (5 mL), is added methoxylamine hydrochloride (0.6 g, 6.86 mmol) and sodium acetate (1.9 g, 22.9 mmol). The mixture is stirred overnight at room temperature and diluted with water. The reaction mixture is extracted three times with EtOAc. The combined EtOAc layer is washed with brine, dried over $MgSO_4$, and concentrated under reduced pressure. The crude product is purified by column eluting with hexane:EtOAc (3:1) to give a mixture of isomers (Z/E) of 8d.

e. The compound of 8d (0.63 g, 1.46 mmol) is mixed with NH2OK (8 mL, 7.4 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by column eluting with $CH_2Cl_2$ to 5% $CH_3OH/CH_2Cl_2$ to give Example 8.

Example 9

Preparation of N-Hydroxy-1N-(4-pyridyloxyphenyl) sulfonyl-4-(Z,E-N-methoxyimino)pyrrolidine-2R-carboxamide a. cis-Hydroxy-D-proline methyl ester (9a): To a solution of cis-Hydroxy-D-proline (6 g, 45.8 mmol) in methanol (50 mL) is added thionyl chloride (17 mL, 229 mmol) dropwise. The mixture is stirred overnight at room temperature. The solvent is removed under reduced pressure to give 9a.

b. Methyl-1N-(4-pyridyloxyphenyl)sulfonyl-4R-hydroxy-pyrrolidine-2R-carboxylate (9b): To a solution of cis-4-hydroxy-D-proline methyl ester 9a (8.5 g, 45.8 mmol) in dioxane (50 mL), water (50 mL) and triethyl amine (26 mL, 184 mmol) at 0° C. is added 4-pyridyloxybenzene sulfonyl chloride (13.0 g, 48 mmol) slowly. The mixture is stirred overnight at room temperature and diluted with 1N HCl. The reaction mixture is extracted three times with EtOAc. The combined EtOAc layer is washed with brine, dried over $MgSO_4$, and concentrated under reduced pressure to give 9b.

c. Methyl-1N-(4-pyridyloxyphenyl)sulfonyl-4-oxo-pyrrolidine-2R-carboxylate (9c): To a solution of alcohol 9b (1.0 g, 2.6 mmol) in acetone (10 mL) is added Jone's reagent (2 mL, 16 mmol, 8N solution prepared as described in Oxidation in Org. Chem., Vol 186, P273). The mixture is stirred overnight at room temperature. The green solid formed is removed by filtration and the solvent removed under reduced pressure. The reaction mixture is then dissolved in NaHCO3 aqueous solution and extracted three times with EtOAc. The combined EtOAc layer is washed with brine, dried over $MgSO_4$, and concentrated under reduced pressure to give 9c.

d. Methyl-1N-(4-pyridyloxyphenyl)sulfonyl-4-(Z,E-N-methoxyimino)pyrrolidine-2R-carboxylate (9d): To a solution of ketone 9c (0.35 g, 0.93 mmol) in dioxane (5 mL), methanol (2 mL) and water (2 mL), is added methoxylamine hydrochloride (0.35 g, 2.79 mmol, 30% w/w in $H_2O$) and sodium acetate (0.76 g, 9.3 mmol). The mixture is stirred overnight at room temperature and diluted with water. The reaction mixture is extracted three times with EtOAc. The combined EtOAc layer is washed with brine, dried over $MgSO_4$, and concentrated under reduced pressure to give 9d as a white solid.

e. The compound of 9d (0.38 g, 0.93 mmol) is mixed with NH2OK (4.4 mL, 7.4 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by reverse phase prep HPLC (90A10B, A, 95% $H_2O$, 5% acetonitrile, 0.1% formic acid; B, 80% acetonitrile, 20% $H_2O$; 19×300 mm waters SymmetryPrep C18 column) to give Example 9 as a white foaming solid.

Example 10

Preparation of N-Hydroxy 1N-(4-n-butoxyphenyl) sulfonyl-4-(Z,E-N-ethoxyimino)pyrrolidine-2R-carboxamide:

a. Methyl-1N-(4-n-butoxyphenyl)sulfonyl-4-(Z,E-N-ethoxyimino)pyrrolidine-2R-carboxylate (10a): To a solution of 2a (1.0 g, 2.82 mmol) in dioxane (10 mL), and methanol (5 mL), is added o-ethylhydoxylamine hydrochloride (0.82 g, 8.45 mmol) and sodium acetate (2.3 g, 28.2 mmol). The mixture is stirred overnight at room temperature and diluted with water. The reaction mixture is extracted three times with EtOAc. The combined EtOAc layer is washed with brine, dried over $MgSO_4$, and concentrated under reduced pressure to give a mixture of isomers (Z/E) of 10a.

b. The compound of 10a (0.5 g, 1.26 mmol) is mixed with NH2OK (6.7 mL, 10 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by reverse phase prep HPLC (45A55B, A, 95% $H_2O$, 5% acetonitrile, 0.1% formic acid; B, 80% acetonitrile, 20% $H_2O$; 19×300 mm waters SymmetryPrep C18 column) to give Example 10.

Example 11

Preparation of N-Hydroxy 1N-(4-Methoxyphenyl) sulfonyl-4-(Z,E-N-tert-butoxyimino)pyrrolidine-2R-carboxamide a. Methyl-1N-(4-methoxyphenyl)sulfonyl-4-(Z,E-N-tert-butoxyimino)pyrrolidine-2R-carboxylate (11a): To a solution of 1a (5.0 g, 15.96 mmol) in dioxane (50 mL), methanol (15 mL) and water (5 mL), is added o-(tert-butyl) hydoxylamine hydrochloride (5.0 g, 40 mmol) and sodium acetate (13 g, 160 mmol). The mixture is stirred overnight at room temperature and diluted with water. The reaction mixture is extracted three times with EtOAc. The combined EtOAc layer is washed with brine, dried over $MgSO_4$, and concentrated under reduced pressure to give a mixture of isomers (Z/E) of 11a.

b. The compound of 11a (0.4 g, 1.04 mmol) is mixed with NH2OK (6 mL, 8 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by reverse phase prep HPLC (45A55B, A, 95% $H_2O$, 5% acetonitrile, 0.1% formic acid; B, 80% acetonitrile, 20% $H_2O$; 19×300 mm waters SymmetryPrep C18 column) to give Example 11.

Example 12

Preparation of N-Hydroxy 1N-(4-n-butoxyphenyl)sulfonyl-4-(Z,E-N-t-butoxyimino)pyrrolidine-2R-carboxamide a. Methyl-1N-(4-n-butoxyphenyl)sulfonyl-4-(Z,E-N-t-butoxyimino)pyrrolidine-2R-carboxylate (12a): To a solution of 2a (1.50 g, 4.23 mmol) in 1,4-dioxane (15 mL), methanol (5 mL), and water (5 mL), is added t-butoxyamine hydrochloride (1.59 g, 12.7 mmol) and sodium acetate (3.49 g, 42.5 mmol). This mixture is stirred overnight at room temperature. The reaction mixture is diluted with water and extracted three times with EtOAc. The combined organic extracts are washed with saturated aq. NaCl, dried over $Na_2SO_4$, filtered, and concentrated under reduced pressure. The crude product is purified by column chromatography (silica gel, 15% EtOAc/hexanes) to give the desired product as a mixture of isomers (Z/E) of 12a.

b. The compound of 12a (1.07 g, 2.51 mmol) is treated with NH2OK solution (11.1 mL, 20 mmol, 1.8 M in methanol) and stirred for 4 hours at room temperature. The reaction is cooled in an ice bath, acidified with 1N aq. HCl, and extracted three times with EtOAc. The combined organic extracts are dried over $Na_2SO_4$, filtered, and concentrated under reduced pressure. The crude product is purified by column chromatography (silica gel, 4% $CH_3OH/CH_2Cl_2$) to give Example 12 as a mixture of isomers (Z/E).

Example 13

Preparation of N-Hydroxy1N-[4-(4-fluorophenoxy)phenyl]sulfonyl-4-(Z,E-N-tert-butoxyimino)-pyrrolidine -2R-carboxamide a. Methyl-1N-[4-(4-fluorophenoxy)phenyl]sulfonyl-4-(Z,E-N-tert-butoxymino)pyrrolidine-2R-carboxylate (13a): To a solution of 8c (0.82 g, 2.08 mmol) in dioxane (8 mL), methanol (5 mL) and water (5 mL), are added o-(tert-butyl) hydoxylamine hydrochloride (0.78 g, 6.25 mmol) and sodium acetate (1.7 g, 20.8 mmol). The mixture is stirred overnight at room temperature, and diluted with water. The reaction mixture is extracted three times with EtOAc. The combined EtOAc layer is washed with brine, dried over $MgSO_4$, and concentrated under reduced pressure to give a mixture of isomers (Z/E) of 13a.

b. The compound of 13a (0.95 g, 2.08 mmol) is mixed with NH2OK (10 mL, 16.6 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by column eluting with 5% $CH_3OH/CH_2Cl_2$ to give Example 13.

Examples 14–15

The following chart shows the structure of compounds exemplified in Examples 14 and 15:

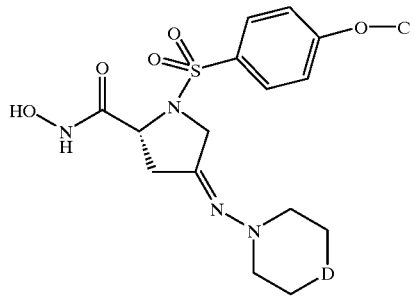

| Example | C | D |
|---|---|---|
| 14 | —$CH_2CH_2CH_2CH_3$ | —$CH_2$ |
| 15 | —$CH_2CH_2CH_2CH_3$ | —O |

—O—C corresponds to a substituent of $R_2$ in Formula (I) when $R_2$ is phenyl.
D corresponds to a member of the heterocycloalkyl ring radical when Z of Formula (I) is N—W and W is heterocylocalkyl.

Example 14

Preparation of N-Hydroxy-1N-(4-n-butoxyphenyl)sulfonyl-4-(Z,E-N-piperidineimino)pyrrolidine-2R-carboxamide a. Methyl-1N-(4-n-butoxyphenyl)sulfonyl-4-(Z,E-N-piperidineimino)pyrrolidine-2R-carboxylate (14a): To a solution of 2a (2.5 g, 7.04 mmol) in dioxane (20 mL) and methanol (15 mL) is added 1-aminopiperidine (1.14 mL, 10.56 mmol) and sodium acetate (5.7 g, 70 mmol). The mixture is stirred overnight at room temperature and diluted with water. The reaction mixture is extracted three times with EtOAc. The combined EtOAc layer is washed with brine, dried over $MgSO_4$, and concentrated under reduced pressure to give 14a.

b. The compound of 14a (0.65 g, 1.49 mmol) is mixed with $NH_2OK$ (4.4 mL, 7.45 mmol, 1.7 M in methanol) and stirred overnight at room temperature. Acidified with 1N HCl, the mixture is extracted three times with EtOAc. The combined EtOAc layer is dried over $MgSO_4$ and concentrated under reduced pressure. The crude product is purified by column eluting with $CH_3OH/CH_2Cl_2$ (5:95) to give Example 14.

Example 15

Preparation of N-Hydroxy 1N-(4-n-butoxyphenyl)sulfonyl-4-(Z,E-N-morpholineimino)pyrrolidine-2R-carboxamide a. Methyl-1N-(4-n-butoxyphenyl)sulfonyl-4-(Z, E-N-morpholineimino)pyrrolidine-2R-carboxylate (15a): To a solution of 2a (1.5 g, 4.2 mmol) in dioxane (20 mL), methanol (5 mL) and water (5 mL) is added 1-aminomorpholine (0.52 mL, 5.04 mmol) and sodium acetate (3.4 g, 42 mmol). The mixture is stirred overnight at room temperature and diluted with water. The reaction mixture is extracted three times with EtOAc. The combined EtOAc layer is washed with brine, dried over $MgSO_4$, and concentrated under reduced pressure to give 15a.

b. The compound of 15a (2 g, 4.2 mmol) is mixed with $NH_2OK$ (13 mL, 22 mmol, 1.7 M in methanol) and stirred overnight at room temperature. Neutralized with 1N HCl to pH~7, the mixture is concentrated under reduced pressure. The crude product is purified by column eluting with $CH_3OH/CH_2Cl_2$ (5:95) to give Example 15.

Examples 16–49

The following chart shows the structure of compounds exemplified in Examples 16–49:

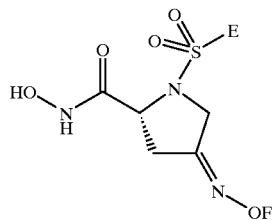

| Example | E | F |
|---|---|---|
| 16 | 4-$NO_2$—$C_6H_4$— | $CH_2CH=CH_2$ |
| 17 | 4-i-BuO—$C_6H_4$— | $CH_2$—$C_6H_4$-p-$CF_3$ |
| 18 | 4-($C_6H_5$)O—$C_6H_4$— | $CH_2$—$C_6H_4$-m-Cl |
| 19 | 4-(4-F—$C_6H_4$)O—$C_6H_4$— | $CH_2$—$C_6H_4$-o-Cl-p-F |
| 20 | 4-(4-Cl—$C_6H_4$)O—$C_6H_4$— | $CH_2$—$C_6H_4$-o-$NO_2$ |
| 21 | 4-(4-Br—$C_6H_4$)O—$C_6H_4$— | $CH_2$—$C_6H_4$-o-OMe |
| 22 | 4-($C_6H_4$)O—$C_6H_4$— | $CH_2$—$C_6H_4$-p-Cl |
| 23 | 4-(O—$C_6H_4$)O—$C_6H_4$— | $CH_2CH_2$—$C_6H_5$ |
| 24 | 4-(4-CN—$C_6H_4$)O—$C_6H_4$— | (4-chloro-1,2,3-thiadiazol-5-yl)methyl |
| 25 | 4-(N—$C_6H_4$)O—$C_6H_4$— | C(O)CH(Ph)CH=CHPh |
| 26 | 4-i-PrO—$C_6H_4$— | (4-phenylpiperazin-1-yl)carbonylmethyl |
| 27 | 4-n-PrO—$C_6H_4$— | $CH_2C(O)NHC_6H_4$-p-Cl |
| 28 | 4-Br—$C_6H_4$— | $CH_2C(O)$morpholinyl |
| 29 | 4-$C_6H_5$—$C_6H_4$— | $CH_2C(O)NHC_6H_4$-o-OMe |
| 30 | 4-(4-F—$C_6H_5$)—$C_6H_4$— | $CH_2C(O)NHCH_2C_6H_4$-p-Cl |
| 31 | 4-(4-Br—$C_6H_5$)—$C_6H_4$— | (2-methyl-1,1-dioxo-tetrahydrothiophen-2-yl)carbonyl |
| 32 | 4-(4-$Me_2$N—$C_6H_4$)—$C_6H_4$— | $CH_2CN$ |
| 33 | 4-(4-CN—$C_6H_4$)—$C_6H_4$— | $CH_2C_6H_5$ |
| 34 | 4-(4-MeO—$C_6H_4$)—$C_6H_4$— | $CH_2C_6H_4$-p-$NO_2$ |
| 35 | 4-(4-$C_5H_4$N)O—$C_6H_4$— | $CH_2CH(CH_3)_2$ |
| 36 | 4-(3-$C_5H_4$N)O—$C_6H_4$— | $CH(CH_3)_2$ |
| 37 | 4-(2-$C_5H_4$N)O—$C_6H_4$— | $CH_2CH=CH_2$ |
| 38 | $C_6H_5CH_2CH_2$— | $CH_2$—$C_6H_4$-p-$CF_3$ |
| 39 | $C_6H_5CH_2$— | $CH_2$—$C_6H_4$-m-Cl |
| 40 | (4-$C_5H_4$N)$CH_2CH_2$— | $CH_2$—$C_6H_4$-o-Cl-p-F |
| 41 | (2-$C_5H_4$N)$CH_2CH_2$— | CH2—$C_6H_4$-o-$NO_2$ |
| 42 | 4-($C_6H_{11}$)O—$C_6H_4$— | $CH_2$—$C_6H_4$-o-OMe |
| 43 | 4-($C_5H_{11}$)O—$C_6H_4$— | $CH_2$—$C_6H_4$-p-Cl |
| 44 | 4-($C_6H_{13}$)O—$C_6H_4$— | $CH_2CH_2$—$C_6H_5$ |
| 45 | 4-($CH_3OCH_2CH_2$)O—$C_6H_4$— | $CH_2CN$ |
| 46 | 5-(2-pyridinyl)-2-thienyl- | $CH_2C_6H_5$ |
| 47 | 5-(3-isoxazolyl)-2-thienyl- | $CH_2C_6H_4$-p-$NO_2$ |
| 48 | 5-(2-(methylthio)pyrimidin-4-yl)-2-thienyl- | $CH_2CH(CH_3)_2$ |
| 49 | 5-(3-(1-methyl-5-(trifluoromethyl)pyrazolyl)-2-thienyl- | $CH(CH_3)_2$ |

E corresponds to $R_2$ in Formula (I).
F corresponds to $R_4$ in Formula (I) when Z is N—$OR_4$.
Me corresponds to methyl ($CH_3$).

Examples 16–49 are prepared using substantially the same procedures as those described in Examples 3–13, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Examples 50–72

The following chart shows the structure of compounds exemplified in Examples 50–72:

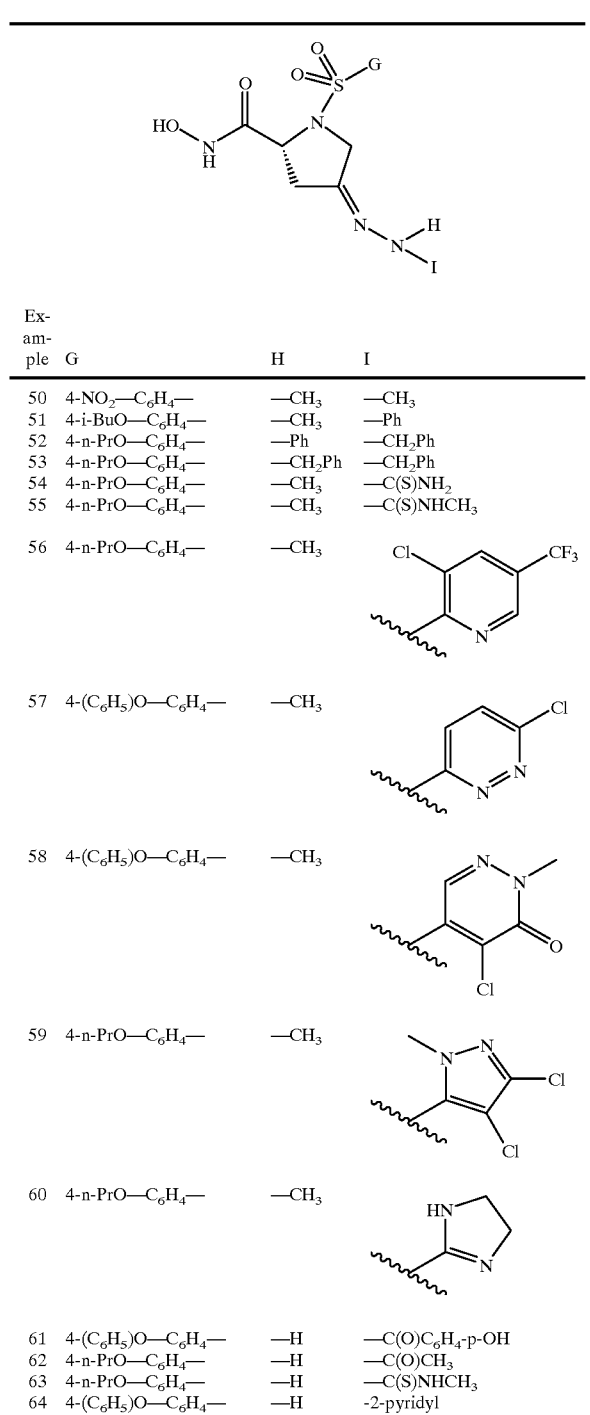

| Example | G | H | I |
|---|---|---|---|
| 50 | 4-$NO_2$—$C_6H_4$— | —$CH_3$ | —$CH_3$ |
| 51 | 4-i-BuO—$C_6H_4$— | —$CH_3$ | —Ph |
| 52 | 4-n-PrO—$C_6H_4$— | —Ph | —$CH_2$Ph |
| 53 | 4-n-PrO—$C_6H_4$— | —$CH_2$Ph | —$CH_2$Ph |
| 54 | 4-n-PrO—$C_6H_4$— | —$CH_3$ | —C(S)$NH_2$ |
| 55 | 4-n-PrO—$C_6H_4$— | —$CH_3$ | —C(S)NH$CH_3$ |
| 56 | 4-n-PrO—$C_6H_4$— | —$CH_3$ | 3-Cl-5-$CF_3$-2-pyridyl |
| 57 | 4-($C_6H_5$)O—$C_6H_4$— | —$CH_3$ | 6-Cl-pyridazin-3-yl |
| 58 | 4-($C_6H_5$)O—$C_6H_4$— | —$CH_3$ | 4-Cl-1-methyl-6-oxo-pyridazin-3-yl |
| 59 | 4-n-PrO—$C_6H_4$— | —$CH_3$ | 3,4-dichloro-1-methyl-pyrazol-5-yl |
| 60 | 4-n-PrO—$C_6H_4$— | —$CH_3$ | 4,5-dihydro-1H-imidazol-2-yl |
| 61 | 4-($C_6H_5$)O—$C_6H_4$— | —H | —C(O)$C_6H_4$-p-OH |
| 62 | 4-n-PrO—$C_6H_4$— | —H | —C(O)$CH_3$ |
| 63 | 4-n-PrO—$C_6H_4$— | —H | —C(S)NH$CH_3$ |
| 64 | 4-($C_6H_5$)O—$C_6H_4$— | —H | -2-pyridyl |
| 65 | 5-(2-pyridinyl)-2-thienyl- | —H | —Ph |
| 66 | 4-n-PrO—$C_6H_4$— | —H | —$CH_2C_6H_5$ |
| 67 | 5-(2-pyridinyl)-2-thienyl- | —H | —C(O)-2-furanyl |
| 68 | 5-(2-pyridinyl)-2-thienyl- | —H | —C(O)-2-thienyl |
| 69 | 4-n-PrO—$C_6H_4$— | —H | —C(O)-2-pyridyl |
| 70 | 4-n-PrO—$C_6H_4$— | —H | —$C_6H_4$-p-$SO_2CH_3$ |
| 71 | 4-(4-$C_5H_4$N)O—$C_6H_4$— | —H | —C(O)$C_6H_5$ |
| 72 | 4-($C_6H_5$)O—$C_6H_4$— | —Ph | —Ph |

G corresponds to $R_2$ in Formula (I).
H and I correspond independently to $R_4$ in Formula (I) when Z is N—$NR_4R_4$.

Examples 50–72 are prepared using substantially the same procedures as those described in Examples 14 and 15, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Examples 73–83

The following chart shows the structure of compounds exemplified in Examples 73–83:

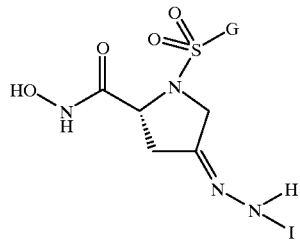

| Example | J | K |
|---|---|---|
| 73 | 4-$NO_2$—$C_6H_4$— | pyrrol-1-yl |

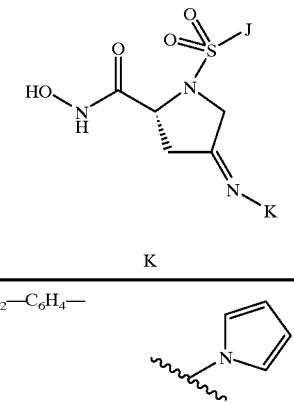

-continued

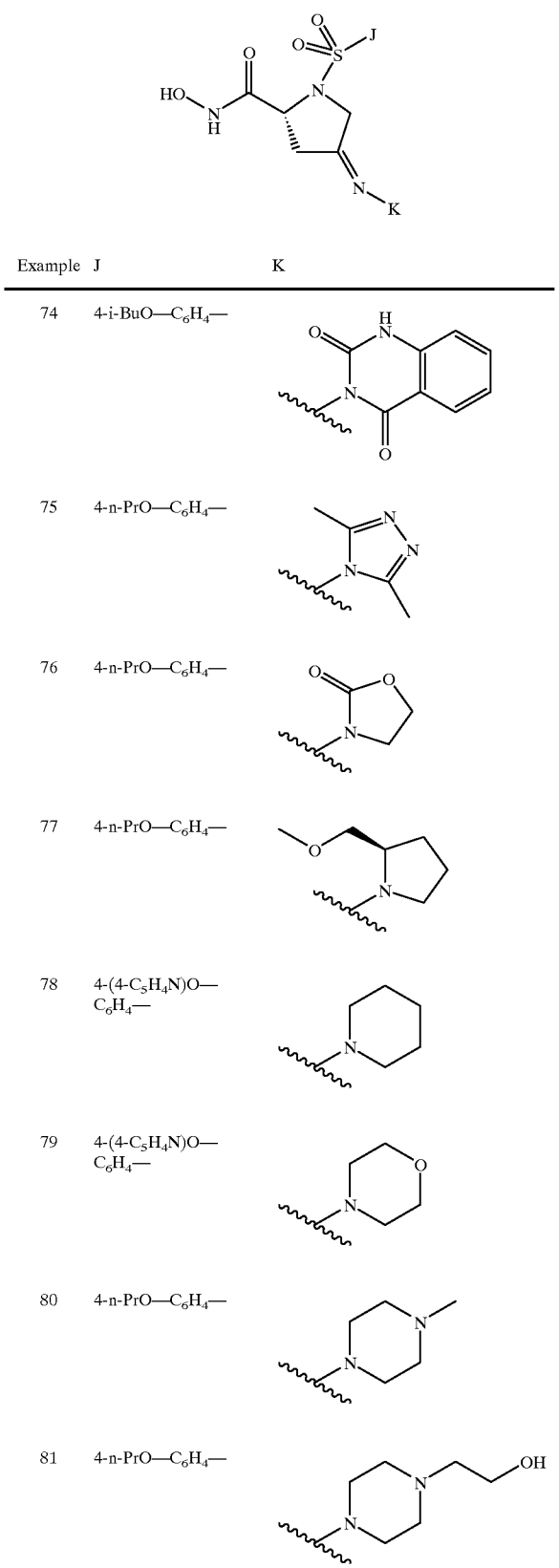

| Example | J | K |
|---|---|---|
| 74 | 4-i-BuO—C$_6$H$_4$— | (quinazoline-2,4-dione) |
| 75 | 4-n-PrO—C$_6$H$_4$— | (dimethyltriazole) |
| 76 | 4-n-PrO—C$_6$H$_4$— | (oxazolidinone) |
| 77 | 4-n-PrO—C$_6$H$_4$— | (2-methoxymethyl-pyrrolidine) |
| 78 | 4-(4-C$_5$H$_4$N)O—C$_6$H$_4$— | (piperidine) |
| 79 | 4-(4-C$_5$H$_4$N)O—C$_6$H$_4$— | (morpholine) |
| 80 | 4-n-PrO—C$_6$H$_4$— | (4-methylpiperazine) |
| 81 | 4-n-PrO—C$_6$H$_4$— | (4-(2-hydroxyethyl)piperazine) |

-continued

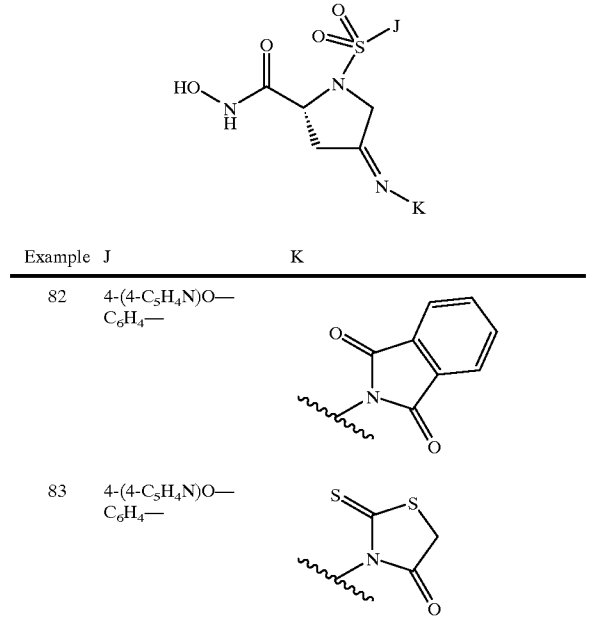

| Example | J | K |
|---|---|---|
| 82 | 4-(4-C$_5$H$_4$N)O—C$_6$H$_4$— | (phthalimide) |
| 83 | 4-(4-C$_5$H$_4$N)O—C$_6$H$_4$— | (2-thioxothiazolidin-4-one) |

J corresponds to R$_2$ in Formula (I).
K corresponds to R$_4$ in Formula (I) when Z is N—NR$_4$R$_4$ and one R$_4$ is hydrogen.

Examples 73–83 are prepared using substantially the same procedures as those described in Examples 14 and 15, substituting the appropriate starting materials. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Example 84

Preparation of N-Hydroxy 1N-(4-methoxyphenyl) sulfonyl-4-methylene-pyrrolidine-2R- carboxamide

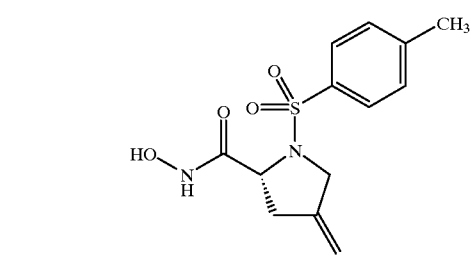

a. Methyl-1N-(4-methoxyphenyl)sulfonyl-4-methylene-pyrrolidine-2R-carboxylate (84a): To a solution of methyl-triphenylphosphonium bromide (1.75 g, 4.78 mmol) in 10 mL of anhydrous THF at 0° C. under argon, is added lithium bis(trimethylsilyl)amide (5.74 mL, 5.74 mmol, 1.0 M solution in THF) dropwise and stirred for 15 minutes. Then, a solution of 1a (1.5 g, 4.78 mmol) in THF (25 mL) is added to it slowly. The mixture is stirred overnight at room temperature and diluted with ammonium chloride. The reaction mixture is extracted three times with EtOAc. The combined EtOAc layer is washed with 1N HCl, water, aqueous NaHCO$_3$, brine, dried over MgSO$_4$, and concentrated under reduced pressure to an oil which is purified by column chromatography eluting with EtOAc/hexane (3/7) to give exomethylene 84a.

b. The compound of 84a (0.26 g, 0.83 mmol) is mixed with NH$_2$OK (3.7 mL, 6.64 mmol, 1.7 M in methanol) and stirred overnight at room temperature. Neutralizeded with 1N HCl, the mixture is extracted three times with EtOAc. The combined EtOAc layer is dried over MgSO$_4$ and concentrated under reduced pressure. The crude product is purified by column eluting with CH2Cl2:CH3OH (95:5) to give Example 84.

Examples 85–91

The following chart shows the structure of compounds exemplified in 85–91:

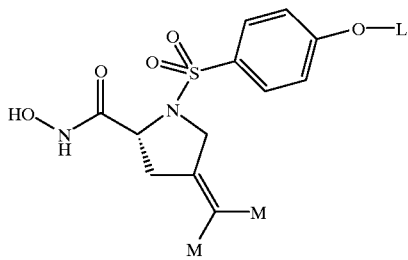

| Example | L | M |
|---|---|---|
| 85 | 4-PhO—C$_6$H$_4$— | —H |
| 86 | 4-n-PrO—C$_6$H$_4$— | —H |
| 87 | 4-(4-C$_5$H$_4$N)O—C$_6$H$_4$— | —CH$_3$ |
| 88 | 4-(4-C$_5$H$_4$N)O—C$_6$H$_4$— | —Cl |
| 89 | 4-(4-C$_5$H$_4$N)O—C$_6$H$_4$— | —F |
| 90 | 4-n-PrO—C$_6$H$_4$— | —CO$_2$Me |
| 91 | 4-n-PrO—C$_6$H$_4$— | —CN |

—O—L corresponds to a substituent of R$_2$ in Formula (I) when R$_2$ is phenyl.
M corresponds to R$_6$ in Formula (I) when Z is CR$_6$R$_6$.

Examples 85–87 are prepared using substantially the same procedure as that described in Example 84, substituting the appropriate starting material. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention. Example 88 is prepared using sequence that includes an olefination procedure (described in J. Chem. Soc. Commun., 1972,, 443). Example 89 is prepared using a sequence that includes an olefination procedure (described in Tetrahedron Lett. 1990, 31, 5571). Example 90 is prepared using a sequence that includes an olefination procedure (described in Tetrahedron, 1993, 49, 6821). Example 91 is prepared using a sequence that includes an olefination procedure (described in J. Am. Chem. Soc., 1962, 84, 3370).

Examples 92–96

The following chart shows the structure of compounds exemplified in 92–96:

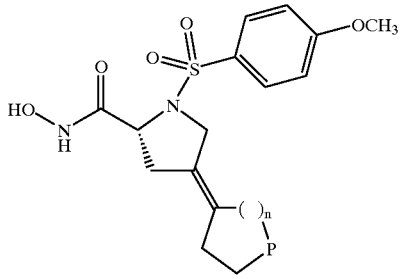

| Example | n | P |
|---|---|---|
| 92 | 1 | —CH$_2$ |
| 93 | 2 | —CH$_2$ |
| 94 | 2 | —O |
| 95 | 2 | —S |
| 96 | 2 | —SO$_2$ |

—O—P corresponds to a member atom of Z in Formula (1) when Z is a ring.

Examples 92–96 are prepared using substantially the same procedure as that described in Example 84 using the appropriately functionalized ylide precursor which is derived from the related bromide precursor. The skilled artisan may change temperature, pressure, atmosphere, solvents or the order of reactions as appropriate. Additionally, the skilled artisan may use protecting groups to block side reactions or increase yields as appropriate. All such modifications can readily be carried out by the skilled artisan in the art of organic chemistry, and thus are within the scope of the invention.

Examples 97–98

The following chart shows the structure of compounds exemplified in Examples 97 and 98:

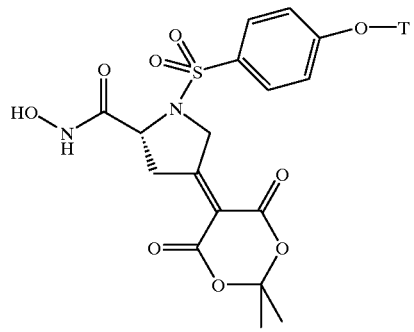

| Example | T |
|---|---|
| 97 | —CH$_2$CH$_2$CH$_3$ |
| 98 | —Ph |

—O—T corresponds to a substituent of R$_2$ in Formula (I) when R$_2$ is phenyl.

Examples 97 and 98 are prepared using a sequence that includes an olefination procedure (described in Synthesis, 1978, 385).

Composition and Method of Use Examples

The compounds of the invention are useful to prepare compositions for the treatment of ailments and the like. The following composition and method examples do not limit the invention, but provide guidance to the skilled artisan to prepare and use the compounds, compositions and methods of the invention. In each case other compounds within the invention may be substituted for the example compound shown below with similar results. The skilled practitioner will appreciate that the examples provide guidance and may be varied based on the condition being treated and the patient.

Example A

A tablet composition for oral administration, according to the present invention, is made comprising:

| Component | Amount |
|---|---|
| The compound of Example 2 | 15. mg |
| Lactose | 120. mg |
| Maize Starch | 70. mg |
| Talc | 4. mg |
| Magnesium Stearate | 1. mg |

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component | Amount (% w/w) |
|---|---|
| The compound of Example 3 | 15% |
| Polyethylene glycol | 85% |

A human male subject weighing 90 kg (198 lbs.), suffering from osteoarthritis, is treated by a method of this invention. Specifically, for 5 years, a capsule containing 70 mg of the compound of Example 3 is administered daily to said subject.

At the end of the treatment period, the patient is examined via orthoscopy, and found to have no further advancement of erosion/fibrillation of the articular cartilage.

Example C

A saline-based composition for local administration, according to the present invention, is made comprising:

| Component | Amount (% w/w) |
|---|---|
| The compound of Example 6 | 5% |
| Polyvinyl alcohol | 15% |
| Saline | 80% |

A patient having deep corneal abrasion applies the drop to each eye twice a day. Healing is speeded, with no visual sequelae.

Example D

A topical composition for local administration, according to the present invention, is made comprising:

| Component | Composition (% w/v) |
|---|---|
| The compound of Example 9 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s. |
| Total = | 100.00 |

A patient suffering from chemical burns applies the composition at each dressing change (b.i.d.). Scarring is substantially diminished.

Example E

A inhalation aerosol composition, according to the present invention, is made comprising:

| Component | Composition (% w/v) |
|---|---|
| Compound of Example 14 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 84 | 0.10 |
| Benzalkonium chloride | 0.01 |
| EDTA | 0.05 |
| Hydroxyethylcellulose (NATROSOL M) | 0.50 |
| Sodium metabisulfite | 0.10 |
| Sodium chloride (0.9%) | q.s. |
| Total = | 100.0 |

A human male subject weighing 90 kg (198 lbs), suffering from corneal ulcerations, is treated by a method of this invention. Specifically, for 2 months, a saline solution containing 10 mg of the compound of Example 84 is administered to said subject's affected eye twice-daily.

Example G

A composition for parenteral administration is made comprising:

| Component | Amount |
| --- | --- |
| The compound of Example 53 | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Example H

A mouthwash composition is prepared;

| Component | % w/v |
| --- | --- |
| The compound of Example 73 | 3.00 |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | balance to 100% |

A patient with gum disease uses 1 ml of the mouthwash thrice daily to prevent further oral degeneration.

Example I

A lozenge composition is prepared;

| Component | % w/v |
| --- | --- |
| The compound of Example 92 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the lozenge to prevent loosening of an implant in the maxilla.

Example J

Chewing Gum Composition

| Component | w/v % |
| --- | --- |
| The compound of Example 2 | 1.00 |
| Sorbitol crystals | 38.44 |
| Paloja-T gum base | 20.00 |
| Sorbitol (70% aqueous solution) | 22.00 |
| Mannitol | 10.00 |
| Glycerine | 7.56 |
| Flavor | 1.00 |

A patient chews the gum to prevent loosening of dentures.

Example K

| Components | w/v % |
| --- | --- |
| Compound of example 3 | 4.0 |
| USP Water | 50.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.0088 |
| Flavor | 0.064 |
| Colorant | 0.0012 |

The composition is prepared by first mixing 80 kg of gylcerin and all of the benzyl alcohol and heating to 65° C., then slowly adding and mixing together methylparaben, propylparaben, water, xanthan gum, and guar gum. Mix these ingredients for about 12 minutes with a Silverson in-line mixer. Then slowly add in the following ingredients in the following order: remaining glycerin, sorbitol, antifoam C, calcium carbonate, citric acid, and sucrose. Separately combine flavors and coolants and then slowly add to the other ingredients. Mix for about 40 minutes. The patient takes the formulation to prevent flare up of colitis.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having the following structure:

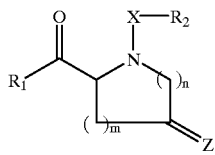

wherein (a) $R_1$ is $NR_3OR_3$, wherein each $R_3$ is independently selected from the group consisting of hydrogen, lower alkyl, and acyl;

(b) X is $SO_2$ or CO;

(c) $R_2$ is selected from the group consisting of hydrogen, alkyl, heteroalkyl, aryl, heteroaryl, cycloalkyl, heterocycloalkyl, aryloxy, and heteroaryloxy;

(d) Z is selected from the group consisting of:
  (i) N—W, wherein n is at least 1 and W is selected from the group consisting of: aryl, heteroaryl, cycloalkyl, and hetcrocycloalkyl;
  (ii) N—$OP_4$, N—$SR_4$, N—$NR_4R_4$, or N—$CR_4R_4R_4$, wherein n is at least 1 and each $R_4$ is independently selected from the group consisting of:
hydrogen, alkyl, heteroalkyl, aryl, heteroaryl, cycloalkyl, and heterocycloalkyl;

(iii)

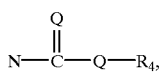

wherein 11 is at least 1 and each Q is independently selected from the group consisting of S and O;

(iv)

N—C(=Q)—$R_4$, wherein n is at least 1;

(v) $CR_6R_6$, wherein each $R_6$ is independently selected from the group consisting of: hydrogen, halo, alkyl, heteroalkyl, aryl, heteroaryl, cycloalkyl, heterocycloalkyl, and cyano;

(vi) a ring, said ring being selected from the group consisting of: cycloalkyl and heterocyloalkyl;

(vii)

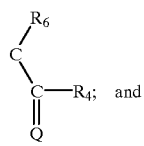

(viii)

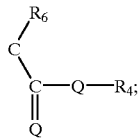

(e) m and n are integers independently selected from 0, 1, or 2 and m+n is 2; and any optical isomer, diastcreomer or enantiomer, or pharmaceutically-acceptable salt, solvate thereof.

2. The compound of claim 1 wherein m and n are each 1.

3. The compound of claim 1 wherein $R_2$ is aryl or heteroaryl.

4. The compound of claim 3 wherein $R_2$ is selected from the group consisting of methoxyphenyl, ethoxyphenyl, propoxyphenyl, butoxyphenyl, pyridyloxyphenyl, and phenoxyphenyl.

5. The compound of claim 4 wherein Z is N—$OR_4$, N—W, $CR_6R_6$, or a ring, said ring being selected from the group consisting of: cycloalkyl and heterocycloalkyl.

6. The compound of claim 5 wherein $R_1$ is NHOH.

7. The compound of claim 6 wherein X is $SO_2$.

8. The compound of claim 7 wherein m and n are each 1.

9. The compound of claim 8 wherein Z is N—$OR_4$ and $R_4$ is hydrogen or alkyl.

10. The compound of claim 9 wherein Z is selected from the group consisting of NOH, $NOCH_3$, $NOCH_2CH_3$, $NOC_4H_9$.

11. The compound of claim 8 wherein Z is $CR_6R_6$ and each $R_6$ is independently hydrogen, halo, or lower alkyl.

12. The compound of claim 8 wherein Z is a ring, said ring being selected from the group consisting of: cycloalkyl and heterocycloalkyl.

13. A pharmaceutical composition comprising:
(a) a safe and effective amount of a compound of claim 1; and
(b) a pharmaceutically-acceptable carrier.

14. A pharmaceutical composition comprising:
(a) a safe and effective amount of a compound of claim 2; and
(b) a pharmaceutically-acceptable carrier.

15. A pharmaceutical composition comprising:
(a) a safe and effective amount of a compound of claim 8; and
(b) a pharmaceutically-acceptable carrier.

16. A pharmaceutical composition comprising:
(a) a safe and effective amount of a compound of claim 11; and
(b) a pharmaceutically-acceptable carrier.

17. A pharmaceutical composition comprising:
(a) a safe and effective amount of a compound of claim 12; and
(b) a pharmaceutically-acceptable carrier.

* * * * *